United States Patent
He et al.

(10) Patent No.: US 10,611,771 B2
(45) Date of Patent: Apr. 7, 2020

(54) PYRAZOLO [3,4-D] PYRIMIDINE DERIVATIVE

(71) Applicant: WEST CHINA HOSPITAL, SICHUAN UNIVERSITY, Chengdu, Sichuan (CN)

(72) Inventors: Yang He, Sichuan (CN); Weimin Li, Sichuan (CN); Li Zhang, Sichuan (CN); Bojiang Chen, Sichuan (CN); Zhixin Qiu, Sichuan (CN)

(73) Assignee: WEST CHINA HOSPITAL, SICHUAN UNIVERSITY, Chengdu, Sichuan (CN)

( * ) Notice: Subject to any disclaimer, the term of this patent is extended or adjusted under 35 U.S.C. 154(b) by 0 days.

(21) Appl. No.: 16/314,364

(22) PCT Filed: Aug. 16, 2016

(86) PCT No.: PCT/CN2016/095504
§ 371 (c)(1),
(2) Date: Mar. 13, 2019

(87) PCT Pub. No.: WO2018/000550
PCT Pub. Date: Jan. 4, 2018

(65) Prior Publication Data
US 2019/0263822 A1 Aug. 29, 2019

(30) Foreign Application Priority Data
Jun. 29, 2016 (CN) .......................... 2016 1 0515065

(51) Int. Cl.
| C07D 487/04 | (2006.01) |
| A61P 35/00 | (2006.01) |
| A61K 31/519 | (2006.01) |
| A61K 31/4985 | (2006.01) |
| C07D 471/04 | (2006.01) |

(52) U.S. Cl.
CPC ........ *C07D 487/04* (2013.01); *A61K 31/4985* (2013.01); *A61K 31/519* (2013.01); *A61P 35/00* (2018.01); *C07D 471/04* (2013.01)

(58) Field of Classification Search
CPC .. C07D 487/04; C07D 471/04; A61K 31/519; A61K 31/4985
See application file for complete search history.

(56) References Cited

FOREIGN PATENT DOCUMENTS

| CN | 102596963 A | 7/2012 |
| WO | 2013102059 A1 | 7/2013 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Gura, Systems for identifying new drugs are often faulty, Science, Nov. 7, 1997, 278(5340): 1041-2.*
Johnson et al., Relationships between drug activity in NCI preclinical in vitro and in vivo models and early clinical trials, Br J Cancer. May 18, 2001, 84(10): 1424-31.*
Simone, Introduction, Omenn, Cancer Prevention, Part XIV. Oncology, Cecil Textbook of Medicine, 20th Edition, vol. 1, pp. 1004-1010 (1996).*
Manuj Tandon et al., "New Pyrazolopyrimidine Inhibitors of Protein Kinase D as Potent Anticancer Agents for Prostate Cancer Cells", PLOS ONE, Sep. 2013, vol. 8, Issue 9, e75601.
Nick Todorovic et al, "Microwave-assisted synthesis of N1- and C3-substituted pyrazolo[3,4-d]pyrimidine libraries", Tetrahedron Letters, 52(2011), pp. 5761-5763.
Apsel, B. et al. "Targeted Polypharmacology: Discovery of Dual Inhibitors of Tyrosine and Phosphoinositide Kinases" Nature Chemical Biology, vol. 4, No. 11, Oct. 12, 2008 (Oct. 12, 2008), pp. 691-699.
Tanaka, M. et al. "An Unbiased Cell Morphology-Based Screen for New, Biologically Active Small Molecules", PLOS Biology, vol. 3, No. 5, Apr. 5, 2005 (Apr. 5, 2005), pp. 764-776.
Schenone, S. et al. "Biologically Driven Synthesis of Pyrazolo[3, 4-d]pyrimidines as Protein Kinase Inhibitors: an Old Scaffold as a New Tool for Medicinal Chemistry and Chemical Biology Studies", Chemical Reviews, vol. 114, May 29, 2014 (May 29, 2014).

* cited by examiner

Primary Examiner — Deepak R Rao
(74) Attorney, Agent, or Firm — Novick, Kim & Lee, PLLC; Allen Xue

(57) ABSTRACT

The present invention discloses pyrazolo[3,4-d]pyrimidine derivatives of formula (I). Compounds provided in the present invention have significant inhibitory effects on tumor cells, can be used for the prevention and/or treatment of tumor-related diseases, especially lung cancer, and have wide application prospects.

12 Claims, 4 Drawing Sheets

PYRAZOLO [3,4-D] PYRIMIDINE DERIVATIVE

TECHNICAL FIELD

Figure 1:
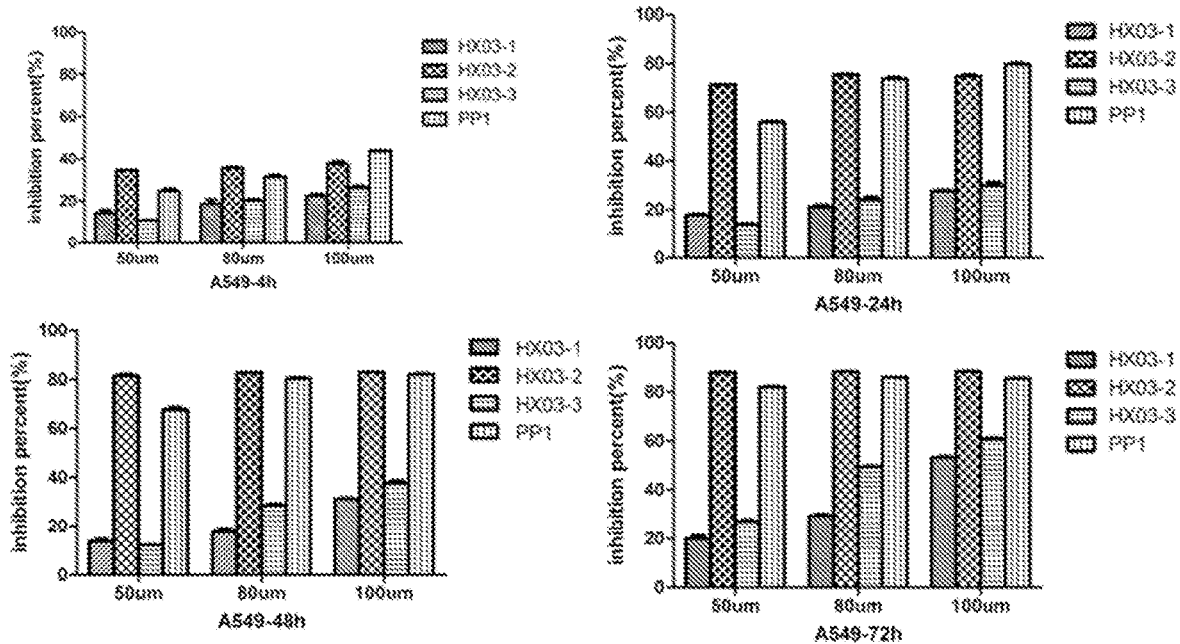

The present invention relates to pyrazolo[3,4-d]pyrimidine derivatives.

BACKGROUND ART

At present, lung cancer is one of the malignant tumors with the fastest growth of morbidity and mortality, as well as the largest threat to population health and life.

However, although there are many kinds of drugs for the treatment of lung cancer on the market, all of them have various defects, such as low bioavailability, bad specificity, great toxic and side effect and so on. While these shortcomings are often due to the structural features of compounds themselves and their targets, that are difficult to overcome in the further study.

Therefore, the persons in this field all hope to synthesize various compounds with different structures, and explore the new targets to overcome above shortcomings.

Content of invention In order to solve above problems, the present invention provides pyrazolo[3,4-d]pyrimidine derivatives with novel structures.

The compounds of formula (I), or the pharmaceutically acceptable salts thereof, or the solvates thereof:

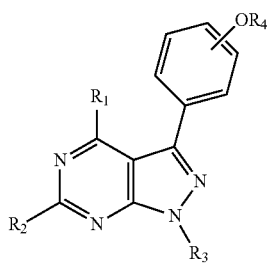

(I)

In which,
$R_1$ represents —$NH_2$, —$NH(C_1$-$C_4$ alkyl) or —$N(C_1$-$C_4$ alkyl)$_2$;
$R_2$ represents hydrogen or $C_1$-$C_6$ alkyl;
$R_3$ represents hydrogen or $C_1$-$C_6$ alkyl;
$OR_4$ represents the substituent in any position of the benzene ring, $R_4$ represents —$(R_5O)_n$—$R_6$—X;
n represents the positive integer of 1~10;
$R_5$ and $R_6$ are independently selected from the group of methylene, ethylidene, propylidene, butylidene, pentylidene, hexylidene, heptylidene, octylidene, nonylidene, or decylidene, respectively;
X represents halogen, —OH, or —$OSO_2$—$R_7$, $R_7$ represents phenyl or phenyl substituted with one or more $C_1$-$C_6$ alkyls;
Further, $R_1$ is —$NH_2$.
Further, $R_2$ is hydrogen.
Further, $R_3$ is $C_1$-$C_6$ alkyl, preferably n-butyl or tert-butyl.
Further, $R_1$ is —$NH_2$, and $R_2$ is hydrogen, and $R_3$ represents $C_1$-$C_6$ alkyl, preferably n-butyl or tert-butyl.
Further, n is 3, 4, or 5.
Further, $R_5$ and $R_6$ are both ethylidenes.
Further, X is p-methylbenzenesulfonyl group.

Further, said compounds are one of the followings:

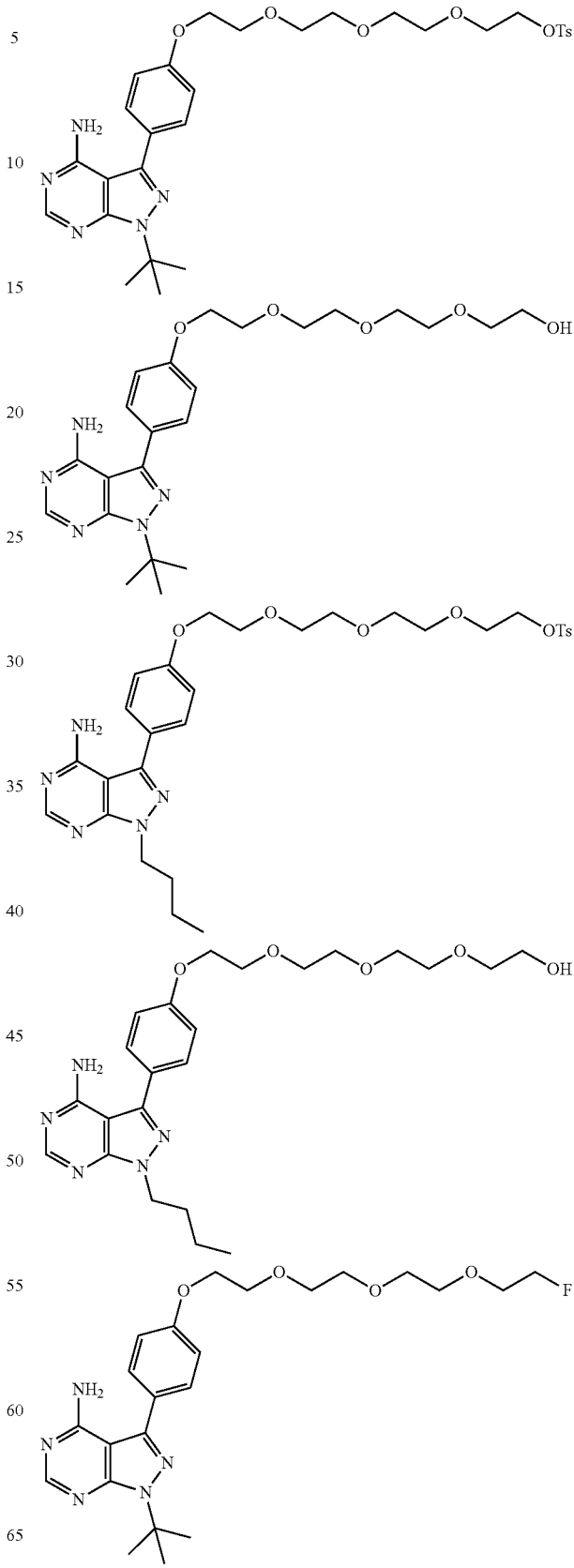

Ts represents p-methylbenzenesulfonyl group.

The present invention also provides the uses of above compounds, or solvates thereof, or pharmaceutically acceptable salts thereof in the preparation of anti-tumor drugs.

Further, said drugs are those for the treatment of lung cancer.

Further, said lung cancer is non-small-cell lung carcinoma.

The present invention also provides a pharmaceutical composition, that is a formulation prepared by using above compounds, or solvates thereof, or pharmaceutically acceptable salts thereof as active constituents, with the addition of pharmaceutically acceptable excipients.

In the present invention, said $C_1$-$C_4$ alkyl means $C_1$, $C_2$, $C_3$, and $C_4$ alkyl, i.e. straight or branch chain alkyl having 1~4 carbons, such as methyl, ethyl, propyl, isopropyl, butyl, isobutyl, tert-butyl, sec-butyl and so on. Similarly, said $C_1$-$C_6$ alkyl means $C_1$, $C_2$, $C_3$, $C_4$, $C_5$, and $C_6$ alkyl, i.e. straight or branch chain alkyl having 1~6 carbons, such as methyl, ethyl, propyl, isopropyl, butyl, isobutyl, tert-butyl, sec-butyl, pentyl, hexyl, and so on.

In the present invention, "treatment" further includes a relapse prevention or a phase prevention, as well as treating acute or chronic signs, symptoms and/or malfunctions. The treatment may be a symptomatic treatment, such as inhibiting symptoms. It can be realized in a short term, regulated in a medium term, or can be mentioned as long term therapy, such as for a maintenance therapy.

Said "prevention" includes delaying and/or preventing the attack of disorders, diseases, or conditions and/or concomitant symptoms thereof; preventing the infection of disorders, diseases, or conditions to the objects; or the methods reducing the risk of objects having disorders, diseases, or conditions. In the present invention, "pharmaceutically acceptable" means a carrier, a vector, a diluent, a adjuvant and/or a resultant salt that can be chemically or physically compatible with other constituents forming certain pharmaceutical dosage form, and physiologically compatible with acceptors.

In the present invention, "salt" means an acid salt and/or basic salt that is formed by a compound or its stereoisomer and inorganic and/or organic acid and base, and also includes amphoteric ion salts (inner salts), and further includes quaternary ammonium salts, such as alkyl ammonium salts. These salts can be directly obtained during the final separation and purification of compounds. These salts can also be obtained by suitably mixing a compound or its steroisomer with a certain amount of acid or base (such as an equivalent amount). These salts may form precipitation in the solution and can be collected by filtration method, or recovered after evaporation of solvent, or prepared by freeze drying after reaction in aqueous medium. In the present invention, said salts can be hydrochlorate, sulfate, citrate, benzenesulphonate, hydrobromate, hydrofluoride, phosphate, acetate, propionate, succinate, oxalate, malate, succinate, fumarate, maleate, tartrate or trifluoroacetate.

Experimental results show that compounds of the present invention have significant inhibitory action on lung cancer cell lines A549 and H1299, with a wide market outlook.

Obviously, based on above content of the present invention, according to the common technical knowledge and the conventional means in the field, without department from above basic technical spirits of the present invention, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

FIGURES

In the following Figures, number hx-03-2 corresponds to compound 2 of the present invention, number hx-03-3 corresponds to compound 4 of the present invention, number hx-03-1 corresponds to compound 5 of the present invention, and pp1 is the positive control drug.

FIG. 1: at different times (4 h, 24 h, 48 h, and 72 h), the inhibitory ratio of HX03-1, HX03-2, HX03-3, and PP1 against A549 at different high concentration (50 μm, 80 μM, and 100 μm).

Figure 2:
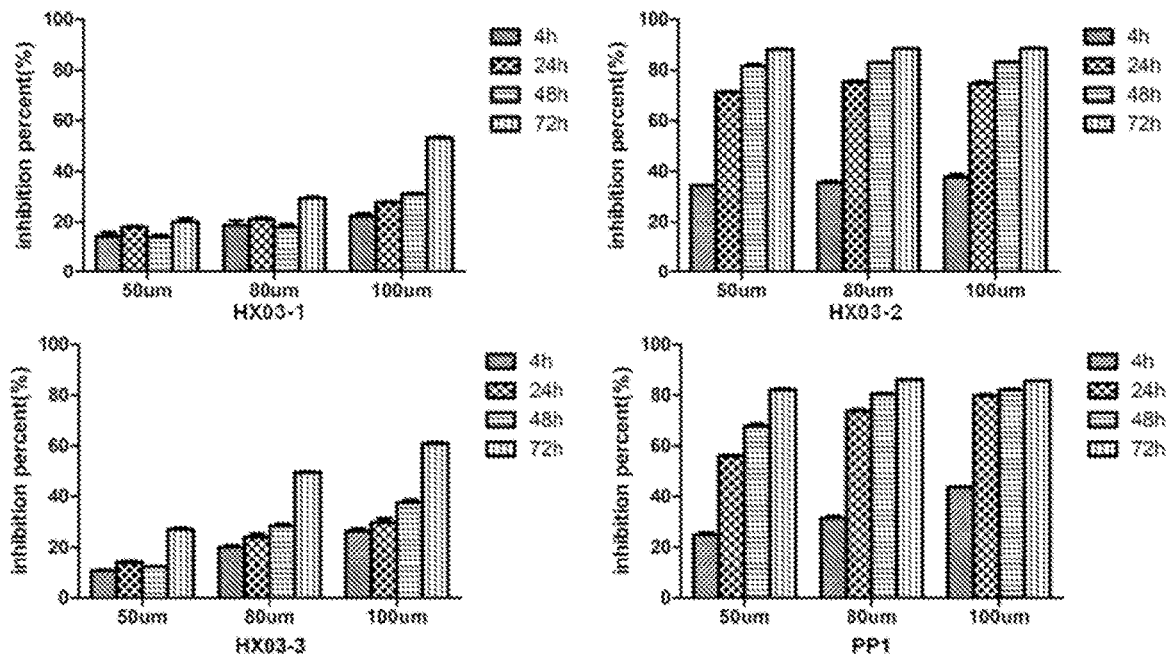

FIG. 2: the inhibitory ratio of HX03-1, HX03-2, HX03-3, and PP1 against A549 at different high concentration (50 μm, 80 μm, and 100 μm) and at different times (4 h, 24 h, 48 h, and 72 h).

Figure 3:
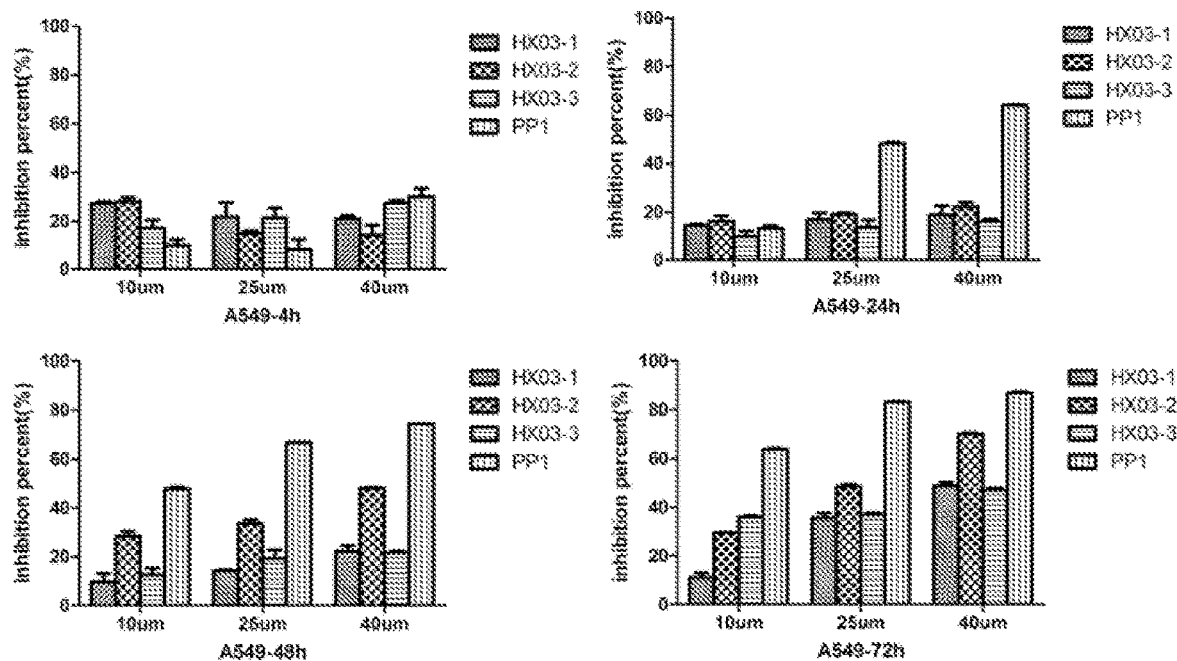

FIG. 3: at different times (4 h, 24 h, 48 h, and 72 h), the inhibitory ratio of HX03-1, HX03-2, HX03-3, and PP1 against A549 at different low concentration (10 μm, 25 μm, and 40 μm).

Figure 4:
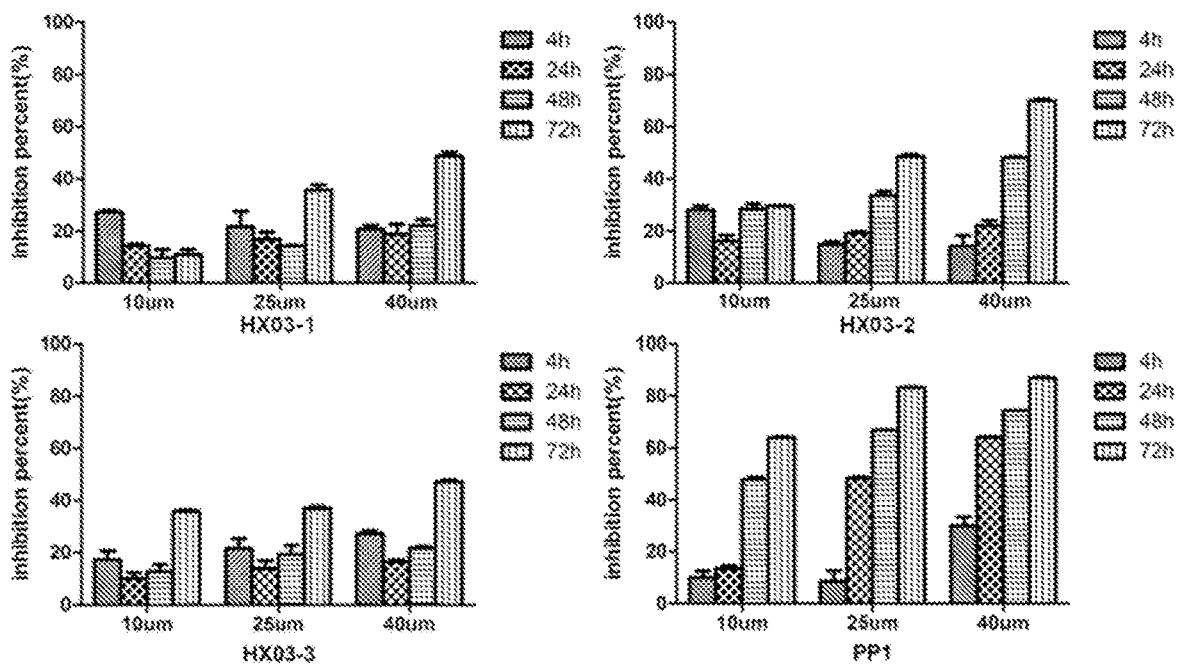

FIG. 4: the inhibitory ratio of HX03-1, HX03-2, HX03-3, and PP1 against A549 at different low concentration (10 μm, 25 μm, and 40 μm) and at different times (4 h, 24 h, 48 h, and 72 h).

Figure 5:
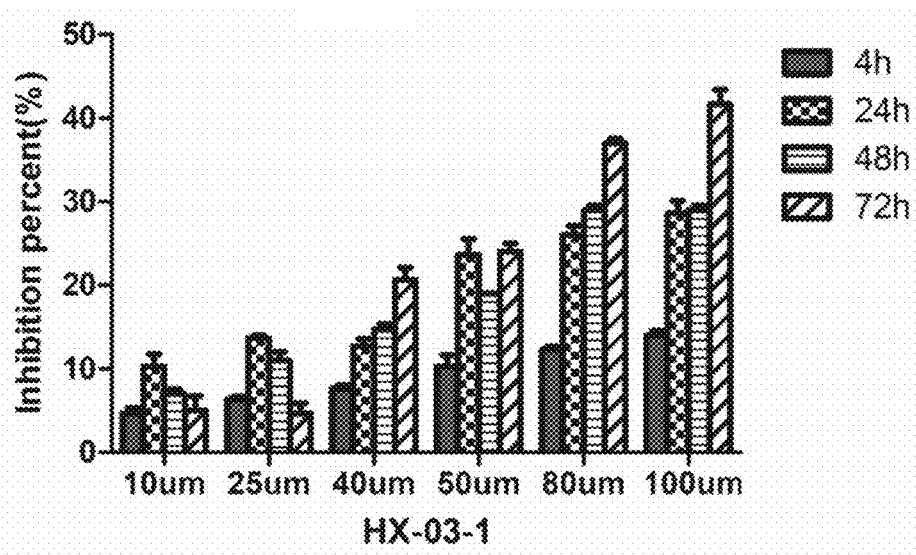

FIG. 5: the inhibitory ratio of HX03-1 against A549 at different high concentration (10 μm, 25 μm, 40 μm, 50 μm, 80 μm, and 100 μm) and at different times (4 h, 24 h, 48 h, and 72 h).

Figure 6:
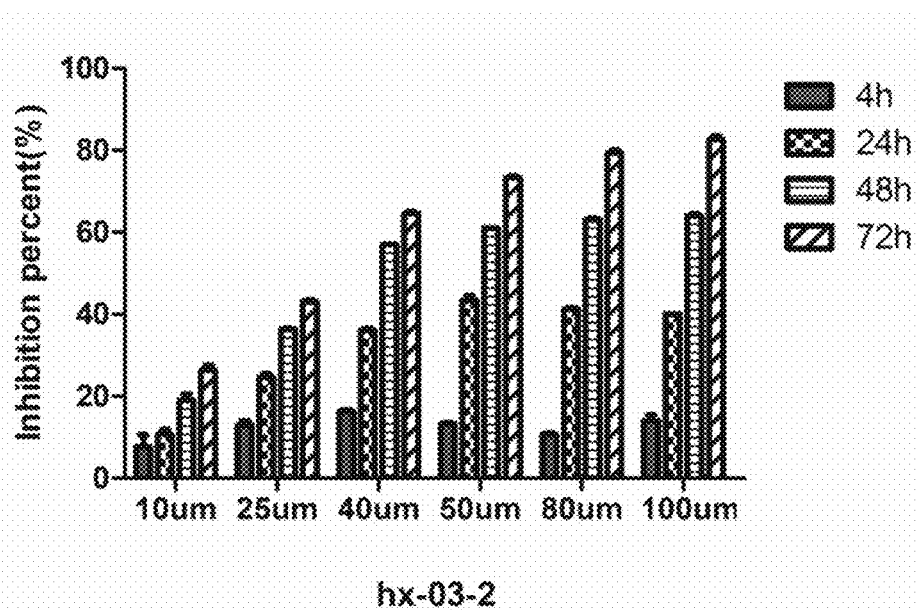

FIG. 6: the inhibitory ratio of HX03-2 against A549 at different high concentration (10 μm, 25 μm, 40 μm, 50 μm, 80 μm, and 100 μm) and at different times (4 h, 24 h, 48 h, and 72 h).

Figure 7:
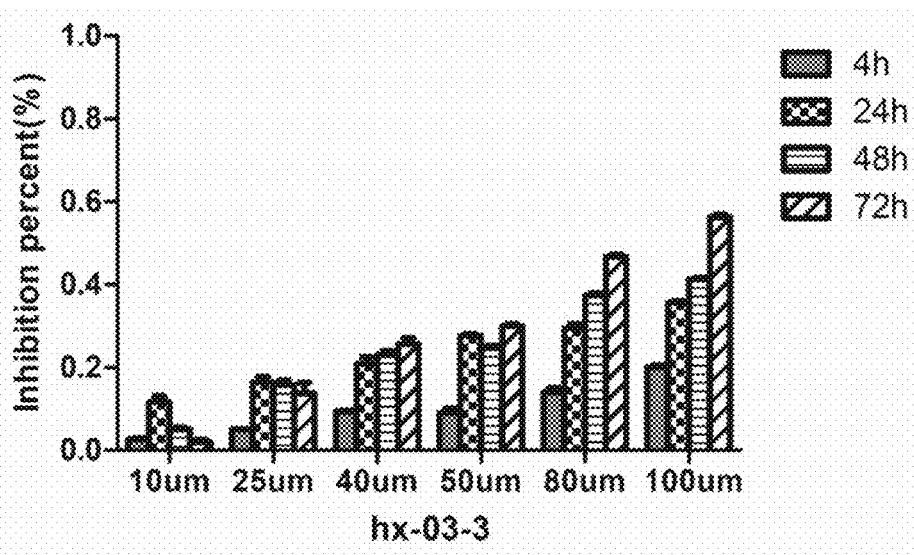

FIG. 7: the inhibitory ratio of HX03-3 against A549 at different high concentration (10 μm, 25 μm, 40 μm, 50 μm, 80 μm, and 100 μm) and at different times (4 h, 24 h, 48 h, and 72 h).

Figure 8:
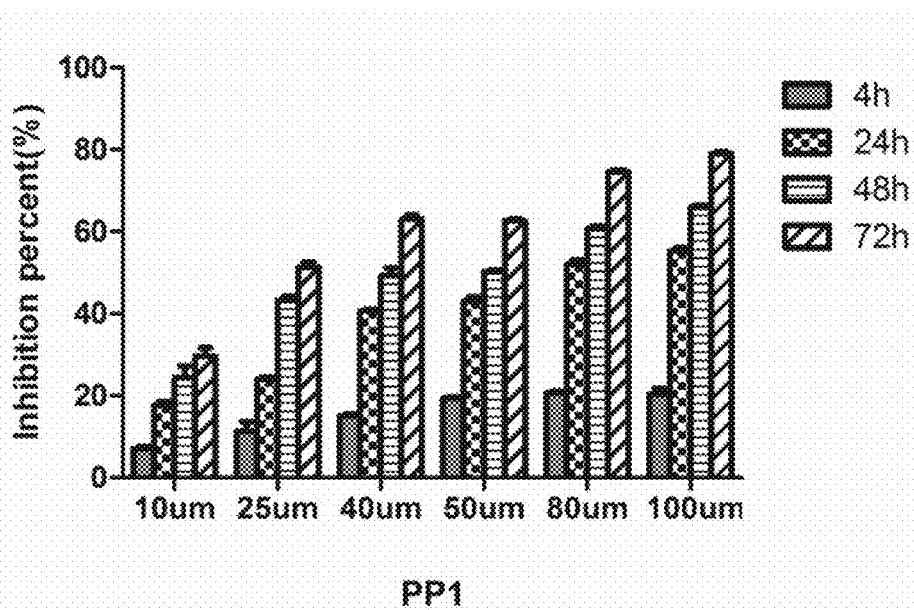

FIG. 8: the inhibitory ratio of PP1 against A549 at different high concentration (10 μm, 25 μm, 40 μm, 50 μm, 80 μm, and 100 μm) and at different times (4 h, 24 h, 48 h, and 72 h).

EXAMPLES

Key intermediate products can be obtained by self-made, while all other reagents used in the synthesis can be purchased from Sinopharm Chemical Reagent Co., Ltd and Changcheng Corporation, respectively.

Example 1 Preparation of Key Intermediates of the Present Invention (1) Preparation of 5-amino-1-tert-butyl-1H-pyrazol-4-cyanogen

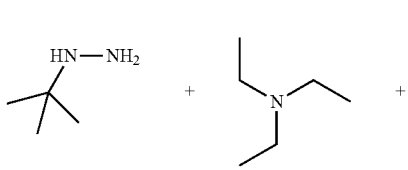

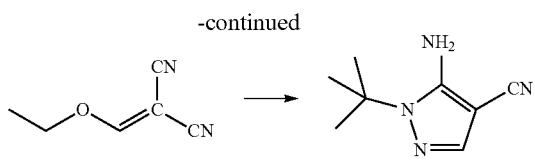

To tert-butylhydrazine hydrochlorate (8.67 g, 69.6 mmol), was added triethylamine (9.7 mL, 69.6 mmol), followed by addition of absolute alcohol (460 mL). After the mixture was dissolved under stirring at room temperature, ethoxymethylenemalononitrile (8.5 g, 69.6 mmol) was added in portions. The solution was refluxed for 3 hours and then cooled. The solvent was evaporated to afford orange solid, that was extracted with ethyl acetate (0.5 L) and water (0.25 L) and dried with MgSO$_4$. The organic layer was evaporated to get orange solid. The resultant solid was continually washed with cyclohexane solution containing 10% ethyl acetate and filtered to provide crystal solid 5-amino-1-tert-butyl 1H-pyrazol-4-cyanogen (9.54 g, yield 83%).

$^1$H NMR (400 MHz, DMSO-d$_6$): δ 7.45 (s, 1H), 6.29 (br s, 2H), 1.51 (s, 9H). HRMS (CI) calcd for C8H12N4 (M) 164.1062, found 164.1080.

(2) Preparation of 1-tert-butyl-1H-pyrazolo[3,4-d]pyrimidin-4-amine

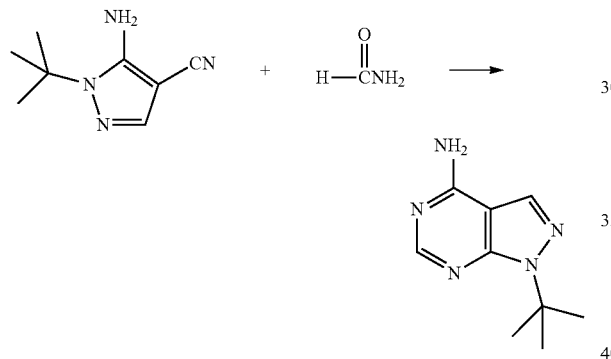

To 5-amino-1-tert-butyl 1H-pyrazolo-4-cyanogen (8, 1.1 g, 1.1 mmol), was added formamide (15 mL), and refluxed for 6 hours. The mixture was extracted with ethyl acetate (3×30 mL), and the resultant organic layer was dried with MgSO$_4$. After filtration, the solvent was evaporated under reduced pressure to provide the brown solid (0.97 g, 0.97 mmol) (yield 77%).

$^1$H NMR (200 MHz, CDCl$_3$): δ 8.31 (s, 1H), 6.33 (b, 2H), 4.40 (t, J=7.2 Hz, 2H), 1.87 (m, 2H), 1.31 (m, 2H), 0.92 (t, J=7.3 Hz, 3H); HR-MS (ESI+): Calc. for [C$_9$H$_{13}$N$_5$]: 192.1205 [M+H]$^+$; Found 192.1251 [M+H]$^+$.

(3) Preparation of 3-bromo-1-tert-butyl-1H-pyrazolo[3,4-d]pyrimidin-4-amine

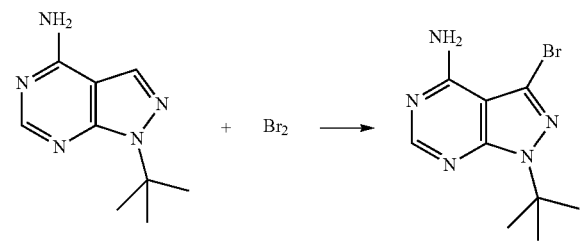

To 1-tert-butyl-1H-pyrazolo[3,4-d]pyrimidin-4-amine (0.97 g, 5.1 mmol) was added 25 mL water, and bromine (0.52 mL, 10.2 mmol) was further added and the mixture was stirred at room temperature for 1 h, then heated at 100° C. for 2 h. The resultant solid was extracted with ethyl acetate (3×25 mL), and washed with 5% NaHSO$_4$ (25 mL) and NaCl solution (25 mL), respectively. Then, the organic layer was dried with MgSO$_4$, filtered, and concentrated. The solvent was evaporated under reduced pressure to provide peach solid (1.2 g, yield 84%).

$^1$H NMR (200 MHz, CDCl$_3$): δ 8.28 (s, 1H), 6.42 (s, 2H), 1.75 (s, 9H); HR-MS (ESI+): Calc. for [C$_9$H$_{12}$BrN$_5$]: 270.0310 [M+H]$^+$; Found 270.0388 [M+H]$^+$.

(4) Preparation of 4-(4-amino-1-tert-butyl-1H-pyrazolo[3,4-d]pyrimidin-3-)phenol

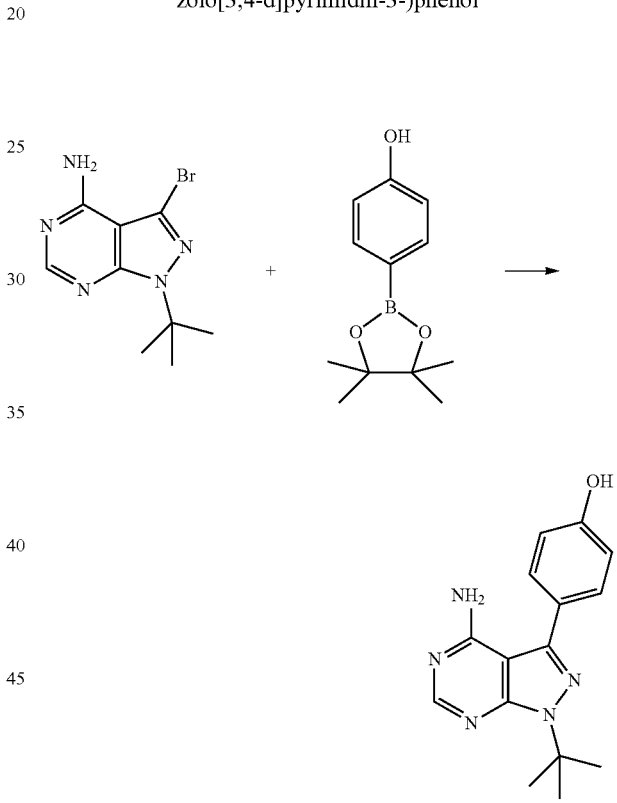

4-(4,4,5,5-Tetramethyl-1,3,2-dioxaborolan-2-yl)phenol (660 mg, 3.0 mmol) was added to the solution of 3-bromo-1-tert-butyl-1H-pyrazolo[3,4-d]pyrimidin-4-amine (150 mg, 0.56 mmol) in 1,4-dioxane/water (5:1, 25 mL: 5 mL), and potassium carbonate (41.4 mg, 3.0 mmol) and pdcl2dppf (4 mg, 0.05 mmol) were continually added. Then, the mixture was heated in oil bath at 90° C. for 2 h and extracted with water and ethyl acetate. The organic layer was dried with anhydrous MgSO$_4$ and evaporated under reduced pressure to provide white solid (100 mg, yield 75%).

$^1$H NMR (600 MHz, DMSO-d$_6$) δ 9.83 (s, 1H, HOAr), 8.28 (s, 1H, CH), 6.97-7.83 (m, 4H, Ar), 1.80 (m, 9H, t-Bu); HR-MS (ESI+): Calc. for [C$_9$H$_{12}$BrN$_5$]: 284.1467 [M+H]$^+$; Found 284.1513 [M+H]$^+$.

(5) Preparation of 1-n-butyl-3-iodo-1H-pyrazolo[3,4-d]pyrimidin-4-amine

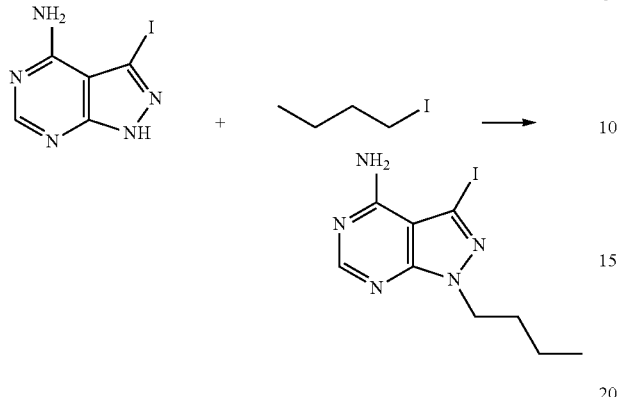

3-Iodo-1H-pyrazolo[3,4-d]pyrimidin-4-amine (2 g, 0.0077 mol) and potassium carbonate (4.2 g, 0.0310 mol) were weighed and added to DMF (50 mL), and after dissolving, the mixture was heated to 90° C. and refluxed, then to the resultant solution was dropped n-butyl iodide (2 mL) by separatory funnel. After reaction for 3 hours, the solvent was evaporated and extracted with ethyl acetate. After dried with anhydrous $Na_2SO_4$, the organic phase was evaporated under reduced pressure, and separated and purified by column chromatography to provide white solid (1.86 g, yield 77%).

$^1$H NMR (200 MHz, $CDCl_3$): δ 8.31 (s, 1H), 6.33 (b, 2H), 4.40 (t, J=7.2 Hz, 2H), 1.87 (m, 2H), 1.31 (m, 2H), 0.92 (t, J=7.3 Hz, 3H); HR-MS (ESI+): Calc. for $[C_9H_{12}IN_5]$: 318.0171 $[M+H]^+$; Found 318.0213 $[M+H]^+$.

(6) Preparation of 4-(4-amino-1-n-butyl-1H-pyrazolo[3,4-d]pyrimidin-3-)phenol

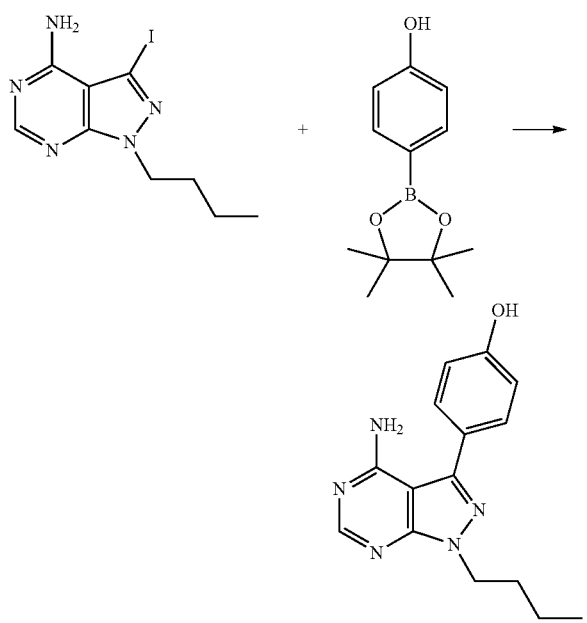

4-(4,4,5,5-Tetramethyl-1,3,2-dioxaborolan-2-yl)phenol (660 mg, 3.0 mmol) was added to the solution of 3-iodo-1-tert-butyl-1H-pyrazolo[3,4-d]pyrimidin-4-amine (180 mg, 0.56 mmol) in 1,4-dioxane/water (5:1, 25 mL:5 mL), followed by addition of potassium carbonate (41.4 mg, 3.0 mmol) and pdcl2dppf (4 mg, 0.05 mmol). Then, the mixture was heated in oil bath at 90° C. for 2 h and extracted with water and ethyl acetate. The organic layer was dried with anhydrous $MgSO_4$ and evaporated under reduced pressure to provide white solid (123 mg, yield 77%).

$^1$H NMR (600 MHz, DMSO-$d_6$): δ 9.75 (s, 1H, HOAr), 8.20 (s, 1H, CH), 6.89-7.46 (m, 4H, Ar—H), 4.28 (t, 2H, $CH_2$), 1.78 (m, 2H, J=6.0 Hz, $CH_2$), 1.22 (m, 2H, J=6.0 Hz, $CH_2$), 0.86 (t, 3H, J=6.0 Hz, $CH_3$); HR-MS (ESI+): Calc. for $[C_9H_{12}BrN_5]$: 284.1467 $[M+H]^+$; Found 284.1513 $[M+H]^+$.

Example 2 Preparation of 2-(2-(2-(2-(4-(4-amino-1-tert-butyl-1H-pyrazolo[3,4-d]pyrimidin-3-)phenoxy)ethoxy)ethoxy)ethoxy)ethyl 4-methylbenzenesulfonic Acid (Compound 1)

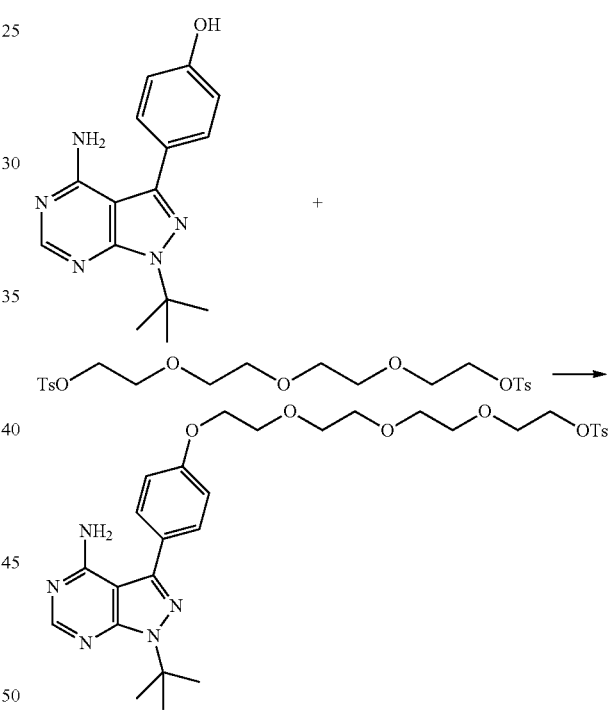

The solution of tetraethylene glycol di-p-tosylate (164 mg, 3.46 mmol), 4-(4-amino-1-tert-butyl-1H-pyrazolo[3,4-d]pyrimidin-3-)phenol (100 mg, 3.46 mmol) and anhydrous potassium carbonate (100 mg, 3.46 mol) in 50 mL benzene was refluxed for 4 h, and after neutralized with 1N HCl, the reaction mixture was extracted with $CH_2Cl_2$. Then, the solution was concentrated under reduced pressure to provide the solid, that was separated by column chromatography to obtain brown syrup product (160 mg, yield 76%).

$^1$H NMR (600 MHz, DMSO-$d_6$): δ 8.23 (s, 1H, CH), 7.09-7.79 (4H, m, arom-H), 3.46-4.14 (m, 16H, $CH_2$—$CH_2$), 2.40 (s, 3H, $CH_3$), 1.74 (S, 9H, t-bu); HR-MS (ESI+): Calc. for $[C_{30}H_{39}N_5O_7S]$: 614.2604 $[M+H]^+$; Found 614.2646 $[M+H]^+$, 634.2469 $[M+Na]^+$, 652.2216 $[M+K]^+$.

Example 3 Preparation of 2-(2-(2-(2-(4-(4-amino-1-n-butyl-1H-pyrazolo[3,4-d]pyrimidin-3-)phenoxy) ethoxy) ethoxy) ethoxy)ethyl 4-methylbenzenesulfonic Acid (Compound 2)

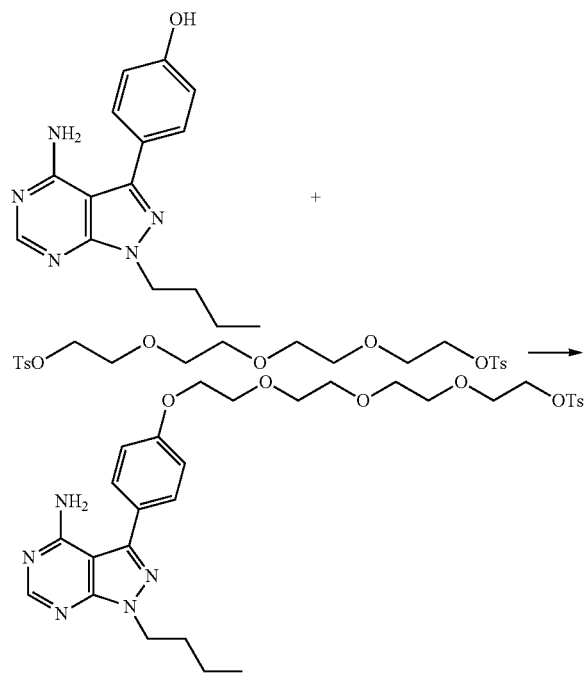

The solution of tetraethylene glycol di-p-tosylate (164 mg, 3.46 mmol), 4-(4-amino-1-n-butyl-1H-pyrazolo[3,4-d]pyrimidin-3-)phenol (100 mg, 3.46 mmol) and anhydrous potassium carbonate (100 mg, 3.46 mol) in 50 mL benzene was refluxed for 4 h, and after neutralized with 1N HCl, the reaction mixture was extracted with $CH_2Cl_2$. Then, the solution was concentrated under reduced pressure to provide the solid, that was separated by column chromatography to obtain brown syrup product (158 mg, yield 73%).

$^1$H NMR (600 MHz, DMSO-$d_6$): δ 8.239 (s, 1H, CH), 7.09-7.79 (4H, m, arom-H), 4.32 (t, 2H, J=6 Hz, $CH_2$), 3.44-4.16 (m, 16H, $CH_2$—$CH_2$), 2.91 (s, 3H, $CH_3$), 2.40 (t, 3H, $CH_3$), 2.05-2.65 (m, 4H, $CH_2$), 0.88 (t, 2H, $CH_2$). HR-MS (ESI+): Calc. for $[C_{30}H_{39}N_5O_7S]$: 614.2604 $[M+H]^+$; Found 614.2762 $[M+H]^+$.

Example 4 Preparation of 2-(2-(2-(2-(4-(4-amino-1-n-butyl-1H-pyrazolo[3,4-d]pyrimidin-3-)phenoxy) ethoxy) ethoxy) ethoxy)ethanol (Compound 3)

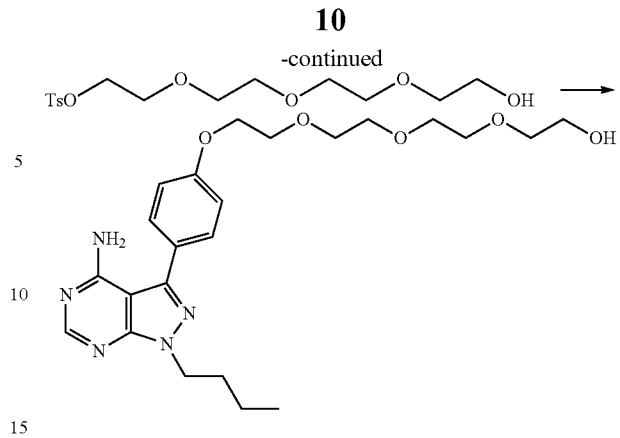

The solution of 2-(2-(2-(2-hydroxyethoxy) ethoxy) ethoxy)ethyl4-methylbenzenesulfonic acid (116 mg, 3.46 mmol), 4-(4-amino-1-n-butyl-1H-pyrazolo[3,4-d]pyrimidin-3-)phenol (100 mg, 3.46 mmol), and anhydrouspotassium carbonate (100 mg, 3.46 mmol) in 50 mL benzene was refluxed for 4 h, and after neutralized with 1N HCl, the reaction mixture was extracted with $CH_2Cl_2$. Then, the solution was concentrated under reduced pressure to provide the solid, that was separated by column chromatography to obtain brown syrup product (130 mg, yield 80%).

Example 5 Preparation of 1-n-butyl-3-(4-(2-(2-(2-(2-fluoroethyl)ethoxy)ethoxy)ethoxy)phenyl)-1H-pyrazolo[3,4-d]pyrimidin-4-amine (Compound 4)

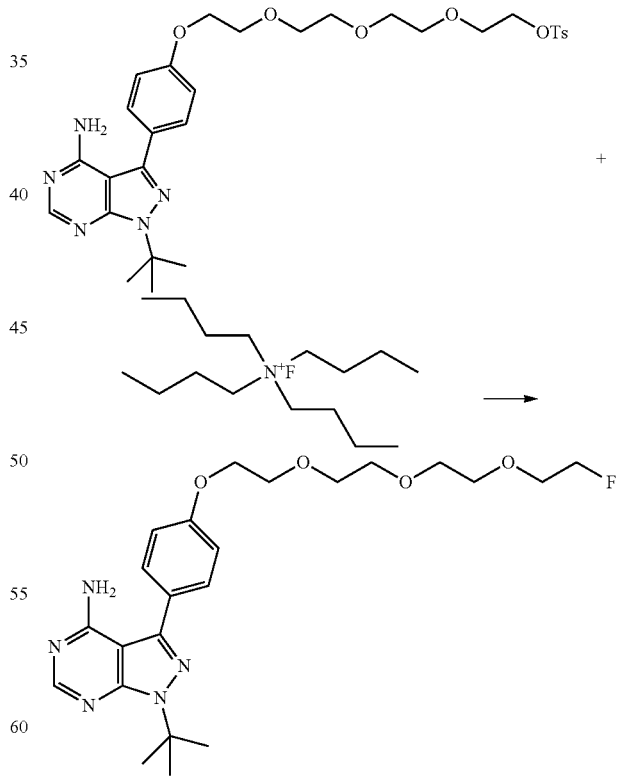

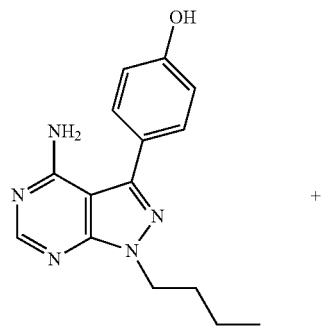

To 20 mL dry THF, was added 2-(2-(2-(2-(4-(4-amino-1-tert-butyl-1H-pyrazolo[3,4-d]pyrimidin-3-)phenoxy) ethoxy)ethoxy)ethyl 4-methylbenzenesulfonic acid (61.3 mg, 0.1 mmol), followed by addition of anhydrous TBAF (1.0 mL, 1 M in THF). The reaction mixture was refluxed for 3 h. After completion of reaction, the solvent was evaporated and extracted with $CH_2Cl_2$. After evaporation of solvent under reduced pressure, the residue was separated and purified by column chromatography to obtain 48 mg product (yield 65%).

$^1$H NMR (600 MHz, DMSO-$d_6$): δ 8.20 (s, 1H, CH), 7.07-7.55 (m, 4H, Ar—H), 3.19-4.53 (m, 16H, $CH_2$), 1.72 (s, 9H, t-Bu); HR-MS (ESI+): Calc. for [$C_{23}H_{32}FN_5O_4$]: 462.2438 [M+H]$^+$; Found 462.2485 [M+H]$^+$.

Example 6 Preparation of 2-(2-(2-(2-(4-(4-amino-1-tert-butyl-1H-pyrazolo[3,4-d]pyrimidin-3-)phenoxy)ethoxy)ethoxy)ethoxy)ethanol (Compound 5)

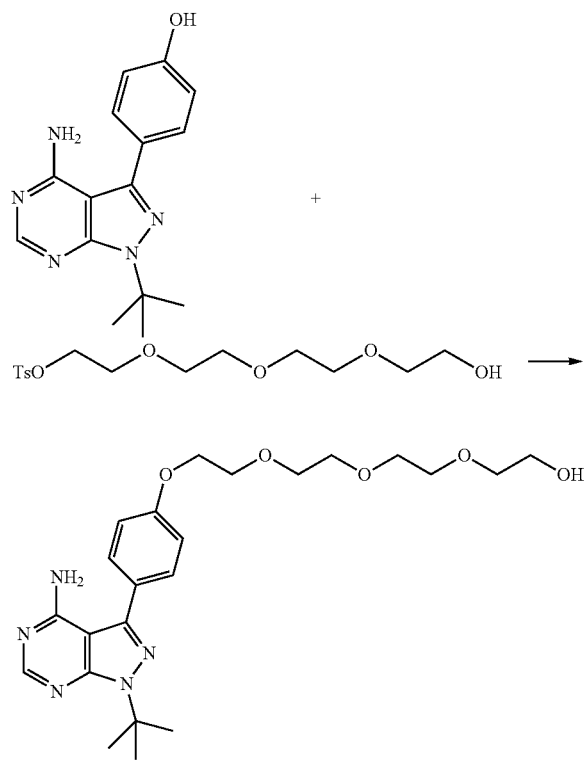

The solution of 2-(2-(2-(2-hydroxyethoxy)ethoxy)ethoxy)ethyl4-methylbenzenesulfonic acid (116 mg, 3.46 mmol), 4-(4-amino-1-tert-butyl-1H-pyrazolo[3,4-d]pyrimidin-3-)phenol (100 mg, 3.46 mmol), and anhydrous potassium carbonate (100 mg, 3.46 mmol) in 50 mL benzene was refluxed for 4 h, and after neutralized with 1N HCl, the reaction mixture was extracted with $CH_2Cl_2$. Then, the solution was concentrated under reduced pressure to provide the solid, that was separated by column chromatography to obtain brown syrup product (132 mg, yield 81%).

$^1$H NMR (600 MHz, DMSO-$d_6$): δ 8.22 (s, 1H, CH), 7.10-7.57 (m, 4H, Ar—H), 4.58 (t, 1H, J=6.0 Hz, OH), 3.41-4.17 (m, 16H, $CH_2$), 5.76 (s, 2H, $NH_2$), 1.74 (s, 9H, t-Bu); HR-MS (ESI+): Calc. for [$C_{23}H_{33}N_5O_5$]: 460.2515 [M+H]$^+$; Found 460.2556 [M+H]$^+$, 482.2379 [M+Na]$^+$.

Example 7 Pharmacodynamic Test of Compounds According to the Present Invention

MTT detection method was used, and MTT is a yellow compound and a dye accepting hydrogen ions, and can be used as the respiratory chain in mitochondria of viable cells. Under the action of succinate dehydrogenase and cytochrome C, the tetrazolium ring broke to form blue formanzan crystal, and the formation amount of formanzan crystal was only directly proportional to the viable counts. The formanzan crystal formed by reduction can dissolve in dimethyl sulfoxide (DMSO), and the optical density (OD) value can be determined at 490 nm using ELISA, to reflect the viable counts.

I. Experimental Procedures
  Lung cancer cell lines: A549 and H1299.
  Experimental materials: lung cancer cell lines, instruments and tools for cell culture, MTT, the compound mother liquid (10 mmol/L), and the positive control drug Src inhibitor pp1.
1. Specific Method
(3-1) Cell lines A549 and H1299 were recovered, and when the cells were in good conditions, namely cells grew to about 80% after one passage (i.e. the logarithmic growth phase), the cells were planked (96-well plate).
(3-2) Firstly, cells were collected, and the concentration of cell suspension was adjusted with counting chamber. Cells were seeded in 96-well plate at 1000~10000 cells/well, and the detailed cell numbers in each well were dependent on the growth rate of different cells and the action time of drugs. A549 cells were seeded at 5000 cells, while H1299 cells were also seeded at 5000 cells, 200 μl for each well (100 μl cell suspension+100 μl drug dilution at different concentration gradient). The edge wells (36) were added 200 μl culture media (for prevention of edge effect).
(3-3) After planking and adding drugs, the plate was treated at 24 h, 48 h, and 72 h, and then for coloration, each well was added 200 μl culture media containing 20 μl MTT solution (5 mg/mL). The plate was continually cultured for 1~4 hours, the incubation was stopped, and the culture supernatant fluid in each well was carefully absorbed. For suspension cells, the culture supernatant fluid in each well need be centrifuged before drawing. 150 μl DMSO was added to each well, and the plate was shaken on a shaking table for 15~20 min, to allow the crystals to be completely dissolved.
(3-4) Colorimetry: The colorimetry was performed by ELISA, and the optical absorption value of each well was tested at a wavelength of 490 nm or 570 nm, and the result was recorded.
(3-5) Calculation Inhibition ratio=(the control−the drug)/the control× 100%

$IC_{50}$ (50% inhibitory concentration) can be calculated by spass software based on the inhibitory ratio at different concentration.

II. Experimental Results
A549 cells were treated at 4 h, 24 h, 48 h, 72 h, and the drug dose was divided into the light concentration group (10 μm, 25 μm, 40 μm) and the high concentration group (50 μm, 80 μm, 100 μm), that were seeded at 6000 cells/well and 5000 cells/well, respectively, to carry out the experiment.

The results were shown in Tables 1~5 and FIGS. 1~4:

TABLE 1

The inhibitory effect of compounds according to the present invention against A549 cells (4 h)

| Compound | Concentration | The inhibitory ratio (%) for three parallel assays | | | The mean inhibitory ratio (%) |
|---|---|---|---|---|---|
| Compound 2 | 10 μm | 25.00 | 30.31 | 29.06 | 28.13 |
|  | 25 μm | 14.38 | 17.19 | 13.44 | 15.00 |
|  | 40 μm | 9.38 | 22.81 | 10.31 | 14.17 |
|  | 50 μm | 34.57 | 34.57 | 34.57 | 34.57 |
|  | 80 μm | 34.86 | 36.86 | 35.14 | 35.62 |
|  | 100 μm | 39.43 | 38.29 | 35.71 | 37.81 |
| Compound 4 | 10 μm | 19.38 | 21.56 | 10.31 | 17.08 |
|  | 25 μm | 27.81 | 13.75 | 22.81 | 21.46 |
|  | 40 μm | 25.94 | 26.56 | 29.69 | 27.40 |
|  | 50 μm | 10.57 | 10.57 | 11.14 | 10.76 |
|  | 80 μm | 20.86 | 20.57 | 18.57 | 20.00 |
|  | 100 μm | 24.29 | 27.14 | 27.43 | 26.29 |
| Compound 5 | 10 μm | 26.88 | 26.25 | 28.75 | 27.29 |
|  | 25 μm | 31.56 | 11.25 | 22.50 | 21.77 |
|  | 40 μm | 23.44 | 20.94 | 18.13 | 20.83 |
|  | 50 μm | 16.57 | 11.14 | 14.57 | 14.10 |
|  | 80 μm | 20.86 | 20.29 | 14.57 | 18.57 |
|  | 100 μm | 24.00 | 20.86 | 22.57 | 22.48 |

TABLE 2

The inhibitory effect of compounds according to the present invention against A549 cells (24 h)

| Compound | Concentration | The inhibitory ratio (%) for three parallel assays | | | The mean inhibitory ratio (%) |
|---|---|---|---|---|---|
| Compound 2 | 10 μm | 16.09 | 20.22 | 12.83 | 16.38 |
|  | 25 μm | 20.43 | 18.48 | 18.70 | 19.20 |
|  | 40 μm | 18.48 | 24.35 | 23.91 | 22.25 |
|  | 50 μm | 71.46 | 71.25 | 71.04 | 71.25 |
|  | 80 μm | 75.63 | 75.83 | 74.79 | 75.42 |
|  | 100 μm | 73.75 | 75.83 | 74.58 | 74.72 |
| Compound 4 | 10 μm | 11.96 | 12.39 | 5.87 | 10.07 |
|  | 25 μm | 19.78 | 10.65 | 10.87 | 13.77 |
|  | 40 μm | 15.00 | 17.39 | 16.52 | 16.30 |
|  | 50 μm | 13.13 | 14.17 | 14.38 | 13.89 |
|  | 80 μm | 25.42 | 25.00 | 21.67 | 24.03 |
|  | 100 μm | 26.67 | 31.25 | 31.46 | 29.79 |
| Compound 5 | 10 μm | 14.35 | 15.65 | 13.26 | 14.42 |
|  | 25 μm | 22.39 | 13.70 | 14.78 | 16.96 |
|  | 40 μm | 26.30 | 16.52 | 14.13 | 18.99 |
|  | 50 μm | 17.08 | 18.33 | 17.92 | 17.78 |
|  | 80 μm | 22.50 | 20.83 | 20.21 | 21.18 |
|  | 100 μm | 27.92 | 27.50 | 27.92 | 27.78 |

TABLE 3

The inhibitory effect of compounds according to the present invention against A549 cells (48 h)

| Compound | Concentration | The inhibitory ratio (%) for three parallel assays | | | The mean inhibitory ratio (%) |
|---|---|---|---|---|---|
| Compound 2 | 10 μm | 24.84 | 31.41 | 29.22 | 28.49 |
|  | 25 μm | 32.66 | 36.72 | 31.56 | 33.65 |
|  | 40 μm | 47.97 | 47.66 | 49.06 | 48.23 |
|  | 50 μm | 82.83 | 81.50 | 80.33 | 81.56 |
|  | 80 μm | 82.67 | 83.00 | 82.83 | 82.83 |
|  | 100 μm | 83.17 | 83.00 | 82.83 | 83.00 |
| Compound 4 | 10 μm | 17.03 | 13.28 | 7.66 | 12.66 |
|  | 25 μm | 12.50 | 21.72 | 23.75 | 19.32 |
|  | 40 μm | 22.50 | 22.03 | 20.31 | 21.61 |
|  | 50 μm | 12.17 | 12.17 | 12.50 | 12.28 |
|  | 80 μm | 27.17 | 28.50 | 29.50 | 28.39 |
|  | 100 μm | 35.50 | 39.00 | 38.17 | 37.56 |
| Compound 5 | 10 μm | 3.13 | 10.94 | 14.84 | 9.64 |
|  | 25 μm | 14.84 | 14.22 | 13.91 | 14.32 |
|  | 40 μm | 19.22 | 26.72 | 20.63 | 22.19 |
|  | 50 μm | 15.33 | 13.33 | 12.83 | 13.83 |
|  | 80 μm | 15.33 | 19.67 | 18.00 | 17.67 |
|  | 100 μm | 30.50 | 31.33 | 31.67 | 31.17 |

TABLE 4

The inhibitory effect of compounds according to the present invention against A549 cells (72 h)

| Compound | Concentration | The inhibitory ratio (%) for three parallel assays | | | The mean inhibitory ratio (%) |
|---|---|---|---|---|---|
| Compound 2 | 10 μm | 30.00 | 29.46 | 29.46 | 29.64 |
|  | 25 μm | 48.74 | 47.21 | 50.00 | 48.65 |
|  | 40 μm | 68.92 | 70.36 | 70.63 | 69.97 |
|  | 50 μm | 88.11 | 87.97 | 88.38 | 88.15 |
|  | 80 μm | 88.51 | 88.38 | 88.51 | 88.47 |
|  | 100 μm | 88.38 | 88.65 | 88.51 | 88.51 |
| Compound 4 | 10 m | 35.32 | 37.12 | 35.77 | 36.07 |
|  | 25 m | 36.40 | 36.04 | 38.65 | 37.03 |
|  | 40 m | 45.86 | 48.20 | 47.48 | 47.18 |
|  | 50 m | 28.38 | 26.49 | 26.22 | 27.03 |
|  | 80 m | 49.46 | 49.05 | 50.00 | 49.50 |
|  | 100 m | 62.03 | 60.27 | 60.41 | 60.90 |
| Compound 5 | 10 m | 9.82 | 8.11 | 15.05 | 10.99 |
|  | 25 m | 35.41 | 32.43 | 39.37 | 35.74 |
|  | 40 m | 50.18 | 45.68 | 50.45 | 48.77 |
|  | 50 m | 20.27 | 17.70 | 22.30 | 20.09 |
|  | 80 m | 29.59 | 28.51 | 30.14 | 29.41 |
|  | 100 μm | 53.11 | 52.70 | 54.05 | 53.29 |

TABLE 5

The inhibitory effect of control drug PP1 against A549 cells (72 h)

| Compound | Concentration | The inhibitory ratio (%) for three parallel assays | | | The mean inhibitory ratio (%) |
|---|---|---|---|---|---|
| PP1 (4 h) | 10 μm | 14.06 | 5.63 | 10.31 | 10.00 |
|  | 25 μm | 16.56 | 3.13 | 5.63 | 8.44 |
|  | 40 μm | 31.88 | 35.00 | 23.44 | 30.10 |
|  | 50 μm | 26.86 | 23.43 | 24.00 | 24.76 |
|  | 80 μm | 32.86 | 31.43 | 30.00 | 31.43 |
|  | 100 μm | 44.00 | 43.43 | 44.00 | 43.81 |
| 24 h | 10 μm | 14.13 | 14.78 | 11.09 | 13.33 |
|  | 25 μm | 49.35 | 47.39 | 48.04 | 48.26 |
|  | 40 μm | 63.91 | 64.13 | 64.35 | 64.13 |
|  | 50 μm | 56.46 | 55.83 | 56.04 | 56.11 |
|  | 80 μm | 74.79 | 72.92 | 73.54 | 73.75 |
|  | 100 μm | 80.63 | 79.58 | 79.17 | 79.79 |
| 48 h | 10 μm | 48.91 | 48.44 | 45.94 | 47.76 |
|  | 25 μm | 66.88 | 67.03 | 66.72 | 66.88 |
|  | 40 μm | 74.53 | 74.22 | 74.53 | 74.43 |
|  | 50 μm | 69.50 | 67.00 | 66.67 | 67.72 |
|  | 80 μm | 81.17 | 80.00 | 80.17 | 80.44 |
|  | 100 μm | 82.50 | 81.33 | 82.33 | 82.06 |
| 72 h | 10 μm | 63.42 | 63.87 | 64.59 | 63.96 |
|  | 25 μm | 83.06 | 82.97 | 83.69 | 83.24 |
|  | 40 μm | 86.76 | 86.13 | 87.66 | 86.85 |
|  | 50 μm | 82.70 | 81.35 | 82.43 | 82.16 |
|  | 80 μm | 85.95 | 86.22 | 86.08 | 86.08 |
|  | 100 μm | 85.41 | 85.68 | 85.68 | 85.59 |

H1299 cells were seeded at 5000 cells/well, and after treatment for 4 h, 24 h, 48 h, and 72 h, the results were shown in Tables 5-9 and FIGS. 5-8:

TABLE 6

The inhibitory effect of compounds according to the present invention against H1299 cells (4 h)

| Compound | Concentration | The inhibitory ratio (%) for three parallel assays | | | The mean inhibitory ratio (%) |
|---|---|---|---|---|---|
| Compound 2 | 10 μm | 9% | 12% | 2% | 7% |
| | 25 μm | 12% | 15% | 12% | 13% |
| | 40 μm | 16% | 17% | 16% | 16% |
| | 50 μm | 14% | 13% | 13% | 14% |
| | 80 μm | 11% | 10% | 11% | 11% |
| | 100 μm | 13% | 17% | 12% | 14% |
| Compound 4 | 10 μm | 3% | 2% | 3% | 3% |
| | 25 μm | 5% | 5% | 5% | 5% |
| | 40 μm | 10% | 9% | 9% | 10% |
| | 50 μm | 11% | 9% | 7% | 9% |
| | 80 μm | 13% | 13% | 16% | 14% |
| | 100 μm | 21% | 20% | 19% | 20% |
| Compound 5 | 10 μm | 4% | 6% | 4% | 4% |
| | 25 μm | 6% | 6% | 7% | 7% |
| | 40 μm | 7% | 8% | 8% | 8% |
| | 50 μm | 13% | 9% | 9% | 10% |
| | 80 μm | 12% | 13% | 12% | 12% |
| | 100 μm | 13% | 15% | 14% | 14% |

TABLE 7

The inhibitory effect of compounds according to the present invention against H1299 cells (24 h)

| Compound | Concentration | The inhibitory ratio (%) for three parallel assays | | | The mean inhibitory ratio (%) |
|---|---|---|---|---|---|
| Compound 2 | 10 μm | 10% | 9% | 13% | 11% |
| | 25 μm | 26% | 23% | 25% | 25% |
| | 40 μm | 36% | 35% | 37% | 36% |
| | 50 μm | 44% | 45% | 41% | 43% |
| | 80 μm | 42% | 41% | 41% | 42% |
| | 100 μm | 40% | 40% | 40% | 40% |
| Compound 4 | 10 μm | 12% | 14% | 9% | 12% |
| | 25 μm | 16% | 19% | 14% | 16% |
| | 40 μm | 18% | 23% | 22% | 21% |
| | 50 μm | 28% | 27% | 28% | 28% |
| | 80 μm | 30% | 27% | 31% | 30% |
| | 100 μm | 36% | 35% | 36% | 36% |
| Compound 5 | 10 μm | 10% | 8% | 13% | 11% |
| | 25 μm | 14% | 13% | 14% | 14% |
| | 40 μm | 11% | 13% | 14% | 13% |
| | 50 μm | 20% | 25% | 26% | 24% |
| | 80 μm | 28% | 26% | 24% | 26% |
| | 100 μm | 29% | 31% | 26% | 28% |

TABLE 8

The inhibitory effect of compounds according to the present invention against H1299 cells (48 h)

| Compound | Concentration | The inhibitory ratio (%) for three parallel assays | | | The mean Inhibitory ratio (%) |
|---|---|---|---|---|---|
| Compound 2 | 10 μm | 16% | 20% | 21% | 19% |
| | 25 μm | 37% | 36% | 36% | 37% |
| | 40 μm | 57% | 57% | 57% | 57% |
| | 50 μm | 61% | 61% | 61% | 61% |
| | 80 μm | 64% | 63% | 62% | 63% |
| | 100 μm | 65% | 64% | 63% | 64% |

TABLE 8-continued

The inhibitory effect of compounds according to the present invention against H1299 cells (48 h)

| Compound | Concentration | The inhibitory ratio (%) for three parallel assays | | | The mean Inhibitory ratio (%) |
|---|---|---|---|---|---|
| Compound 4 | 10 μm | 4% | 5% | 6% | 5% |
| | 25 μm | 15% | 18% | 14% | 16% |
| | 40 μm | 22% | 22% | 25% | 23% |
| | 50 μm | 24% | 24% | 26% | 25% |
| | 80 μm | 36% | 38% | 38% | 37% |
| | 100 μm | 42% | 41% | 41% | 41% |
| Compound 5 | 10 μm | 4% | 5% | 6% | 5% |
| | 25 μm | 15% | 18% | 14% | 16% |
| | 40 μm | 22% | 22% | 25% | 23% |
| | 50 μm | 24% | 24% | 26% | 25% |
| | 80 μm | 36% | 38% | 38% | 37% |
| | 100 μm | 42% | 41% | 41% | 41% |

TABLE 9

The inhibitory effect of compounds according to the present invention against H1299 cells (72 h)

| Compounds | Concentration | The inhibitory ratio (%) for three parallel assays | | | The mean inhibitory ratio (%) |
|---|---|---|---|---|---|
| Compound 2 | 10 μm | 28% | 24% | 27% | 26% |
| | 25 μm | 44% | 43% | 42% | 43% |
| | 40 μm | 65% | 65% | 64% | 65% |
| | 50 μm | 73% | 74% | 73% | 74% |
| | 80 μm | 80% | 80% | 78% | 80% |
| | 100 μm | 84% | 83% | 81% | 83% |
| Compound 4 | 10 μm | 3% | 1% | 3% | 2% |
| | 25 μm | 14% | 18% | 9% | 14% |
| | 40 μm | 23% | 26% | 28% | 26% |
| | 50 μm | 30% | 31% | 29% | 30% |
| | 80 μm | 48% | 46% | 46% | 47% |
| | 100 μm | 55% | 57% | 57% | 56% |
| Compound 5 | 10 μm | 8% | 5% | 2% | 5% |
| | 25 μm | 7% | 4% | 3% | 5% |
| | 40 μm | 18% | 21% | 23% | 20% |
| | 50 μm | 26% | 23% | 23% | 24% |
| | 80 μm | 37% | 36% | 38% | 37% |
| | 100 μm | 45% | 41% | 39% | 42% |

In summary, the compounds provided in the present invention have significant inhibitory effects on tumor cells, can be used for the prevention and/or treatment of tumor-related diseases, especially lung cancer, and have wide application prospects.

The invention claimed is:
1. A compound of formula (I), or a pharmaceutically acceptable salt thereof, or a solvate thereof:

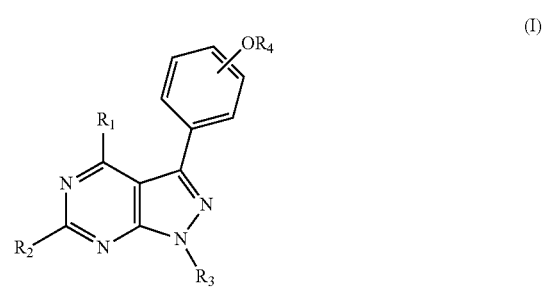

(I)

wherein,
$R_1$ represents —$NH_2$, —$NH(C_1\text{-}C_4$ alkyl$)$ or —$N(C_1\text{-}C_4$ alkyl$)_2$;

R₂ represents hydrogen or $C_1$-$C_6$ alkyl;

R₃ represents hydrogen or $C_1$-$C_6$ alkyl;

—OR₄ represents the substituent in any position on a benzene ring, R₄ represents —$(R_5O_n)$—R₆—X;

n represents a positive integer of 1 to 10;

R₅ and R₆ are independently selected from the group of methylene, ethylidene, propylidene, butylidene, pentylidene, hexylidene, heptylidene, octylidene, nonylidene, and decylidene; and X represents halogen, —OH, or —OSO₂—R₇, R₇ represents phenyl or phenyl substituted with one or more $C_1$-$C_6$ alkyls.

2. The compound according to claim 1, wherein R₁ is —NH₂.

3. The compound according to claim 1, wherein R₂ is hydrogen.

4. The compound according to claim 1, wherein R₃ represents n-butyl or tert-butyl.

5. The compound according to claim 1, wherein R₁ is —NH₂, and R₂ is hydrogen, and R₃ represents n-butyl or tert-butyl.

6. The compound according to claim 1, wherein n is 3, 4, or 5.

7. The compound according to claim 1, wherein R₅ and R₆ are both ethylidenes.

8. Compounds according to claim 1, wherein X is a p-methylbenzenesulfonyl group.

9. The compound according to claim 1 is

[chemical structures]

or

[chemical structures]

wherein Ts represents a p-methylbenzenesulfonyl group.

10. A pharmaceutical composition, comprising one or more selected from the compound, the solvate, and the pharmaceutically acceptable salt of claim 1 as an active constituent and a pharmaceutically acceptable excipient.

11. A method for treating lung cancer, comprising administering the pharmaceutical composition of claim 10 to a subject in need thereof.

12. The method of claim 11, wherein the lung cancer is a non-small cell lung carcinoma.

* * * * *